United States Patent [19]

Hansen et al.

[11] Patent Number: 5,431,692
[45] Date of Patent: Jul. 11, 1995

[54] METHOD AND APPARATUS FOR TESTING COMPATIBILITY OF LEAD POLARITY AND POLARITY PROGRAMMING OF A CARDIAC STIMULATOR

[75] Inventors: Daniel L. Hansen, Aurora; Anthony J. Ujhazy, Denver, both of Colo.

[73] Assignee: Telectronics Pacing Systems, Inc., Englewood, Colo.

[21] Appl. No.: 101,508

[22] Filed: Aug. 2, 1993

[51] Int. Cl.⁶ .................................... A61N 1/362
[52] U.S. Cl. ......................... 607/28; 607/37; 607/27
[58] Field of Search ............. 607/28, 27, 4, 8, 30, 607/32, 9, 37; 128/734

[56] References Cited

U.S. PATENT DOCUMENTS

| | | | |
|---|---|---|---|
| 4,281,664 | 8/1981 | Duggan | 607/32 |
| 4,305,396 | 12/1981 | Wittkampf et al. | 607/11 |
| 4,448,196 | 5/1984 | Money et al. | 128/419 PT |
| 4,532,931 | 8/1985 | Mills | 128/419 PG |
| 4,692,719 | 9/1987 | Whigham | 332/11 D |
| 4,899,750 | 2/1990 | Ekwall | 128/734 |
| 4,901,725 | 2/1990 | Nappholz et al. | 128/419 PG |
| 4,964,407 | 10/1990 | Baker et al. | 128/419 PG |
| 5,003,975 | 4/1991 | Hafelfinger et al. | 607/28 |
| 5,224,475 | 7/1993 | Berg et al. | 607/8 |

*Primary Examiner*—William E. Kamm
*Assistant Examiner*—Kennedy J. Schaetzle
*Attorney, Agent, or Firm*—Gottlieb, Rackman & Reisman

[57] ABSTRACT

A cardiac stimulation device includes a system for testing lead polarity and determining whether the programmed polarity configuration is compatible with an attached pacing and sensing lead. The lead polarity test is based on a measurement of lead impedance performed during the delivery of a pacing pulse. Since the polarity test consists of lead impedance measurements for all polarity configurations, including incompatible configurations, the system provides for backup pacing pulses in a safe configuration to assure pacing support of a patient during all cardiac cycles.

22 Claims, 11 Drawing Sheets

FIG. 6

| | SW 1,2 | SW 3,4 | SW 5,6,7,21 | SW 8 | SW 9 | SW 10 | SW 11,13 | SW 12 | SW 14 | SW 15,16 | SW 17,18 | SW 19,20 | SW 22 | SWM 8 | SWM 14,15 | SWM 16 | SWM 21 | SWM 22 | SWM 23,29,30 | SWM 28 |
|---|---|---|---|---|---|---|---|---|---|---|---|---|---|---|---|---|---|---|---|---|
| SENSING | | SP | C | | | | | | | | | | | | | | | | | C |
| SAMPLE/DISCONNECT TIP | PP | | | | | | | | | | | | | | | | | | | |
| STIMULUS | PP | | | C | | C | C | C | | | C | | | C | C | C | | | | |
| PASSIVE POST CHARGE | PP | | | | C | C | C | C | | | C | | | | C | | | | | |
| BOOST TURN ON | PP | | | | | | C | C | | | C | | C | | C | | | | | |
| ACTIVE POST CHARGE | PP | | | | P | C | C | C | P | | C | | C | | C | | | | | |
| BOOST TURN OFF | PP | | | | | C | C | C | | | C | | | | C | | | | | |
| WARM-UP | | SP | C | | | | C | | | | C | | | C | C | | C | | | |
| DELTA SAMPLE | | SP | C | | | | C | | | | C | | | | C | | C | C | C | |
| CONVERT | | SP | C | | | | C | | | | C | | | | C | | | | C | |
| SENSING | | SP | C | | | | C | | | | C | C | | | | | | | | C |

C = Closed
P = If protect, then SW9=C else SW14=C
PP = If bipolar pacing selected, then SW2=C else SW1=C
SP = If bipolar sensing selected, then SW4=C else SW3=C

METHOD AND APPARATUS FOR TESTING COMPATIBILITY OF LEAD POLARITY AND POLARITY PROGRAMMING OF A CARDIAC STIMULATOR

FIELD OF THE INVENTION

This invention relates to implantable cardiac pacemakers and, more particularly, to a method and apparatus in such a pacemaker for determining that the polarity settings of pacing and sensing circuits within the pacemaker are consistent with the polarity of the lead coupled to the pacemaker.

BACKGROUND OF THE INVENTION

Cardiac pacemakers stimulate a patient's heart by applying current pulses to cardiac tissue via two electrodes, a cathode and an anode. Standard pacing leads exist in either of two configurations, unipolar leads or bipolar leads, depending on the arrangement of the electrodes of a particular lead. A unipolar pacing lead contains a single electrode, normally the cathode, which extends pervenously distal from the pacemaker in an insulating enclosure until it is adjacent to the tip of the lead where the insulation is terminated to provide for electrical contact of the cathode with the heart. The anode provides a return path for the pacing electrical circuit. For a unipolar lead, the anode is the pacemaker case. A bipolar lead contains two electrodes within an insulating sheath, an anode which extends distal from the pacemaker to a position adjacent to but spaced from the electrode tip, and a cathode which also extends distal from the pacemaker but terminates a short distance distal of the anode, at the lead tip. The insulation-exposed anode commonly takes the form of a ring. The cathode and anode of a bipolar lead are separated by an insulating barrier. In present-day pacemakers, circuits for pacing and sensing, which determine tip, ring and case electrode connections, are provided. Thus the pacemakers can be programmed via telemetry for either bipolar or unipolar operation with respect to either sensing or pacing operations.

One problem that persists in present-day pacemakers is that of guaranteeing the pacemaker will not be programmed into a bipolar mode when it is connected to a unipolar lead. A similar problem arises in some rate-responsive pacemakers requiring implantation of a bipolar lead in the heart to sense a physiological parameter which may then be used to determine a metabolic demand pacing rate (see U.S. Pat. No. 4,901,725, entitled "Minute Volume Rate-Responsive Pacemaker", issued to T.A. Nappholz et al. on Feb, 20, 1990). Upon occasion a unipolar lead has been inadvertently implanted with such a rate-responsive pacemaker, and the device has had to be explanted because it failed to rate-respond. A lead polarity test at the time of implant, together with an appropriate warning of the implantation of a lead which is inconsistent with device requirements, could prevent an explantation procedure. Attempts have been made to solve these problems.

In U.S. Pat. No. 4,532,931, entitled "Pacemaker with Adaptive Sensing Means for use with Unipolar or Bipolar Leads", issued on Aug. 6, 1985, P.A. Mills discloses a sensing circuit for a cardiac stimulator capable of automatically adapting to use with either bipolar or unipolar leads without the necessity for telemetric programming of a polarity parameter contained within the implanted pacemaker. The circuit senses artifacts and intrinsic cardiac signals, such as R-waves, on an implanted lead to determine lead polarity. If a unipolar lead is connected to a terminal receptacle of the pacer at the time of implant, the pacer will sense electrical signals between a distal tip electrode and the metal body of the pacemaker. If a bipolar lead is attached to the terminal receptacle at the time of implant, the pacer will sense electrical signals between a tip electrode and a ring electrode spaced a short distance proximal to the distal tip electrode. The pacemaker determines lead polarity through analysis of impedance ratios and voltage division at the input terminals of the pacemakers sensing amplifier. It measures intrinsic activity or artifact signals for both the unipolar and bipolar configurations to determine whether a bipolar lead is present.

One problem with the Mills pacemaker is that it requires the sensing of cardiac electrical signals and artifacts for its analysis. Therefore, the pacemaker requires a lead which is appropriately implanted within the heart and capable of sensing electrical signals within a reasonable range of amplitudes for the polarity test feature to operate in a reliable manner. Furthermore, the pacemaker requires a somewhat appropriate setting of the sensitivity of the amplifiers within the sensing circuit for viable operation.

U.S. Pat. No. 4,964,407, entitled "Method and Apparatus for Assuring Pacer Programming is Compatible with the Lead", issued on Oct. 23, 1990 to R.G. Baker et al. addresses some of the problems of the Mills invention. Baker et al. teaches a pacemaker which employs an internal microprocessor which generates a series of test signals to determine whether a bipolar or unipolar lead is attached to the lead connector of the pacemaker. The pacemaker restricts its telemetric programming to a unipolar mode unless it has detected the presence of a bipolar lead. The pacemaker performs this detection by generating a series of low frequency noise pulses via a high impedance circuit, applying these pulses to lead contacts and sensing a return signal. If a return signal is detected, this indicates either that a unipolar lead is connected to the pacemaker or that the ring conductor of a bipolar lead is open and bipolar pacing must be inhibited.

A disadvantage of the Baker et al. pacemaker is that it requires additional circuitry for generating the test signals. These additional circuits add to the size and energy requirements of the pacemaker. A very important consideration in implanted cardiac pacemakers is restraint of size and energy requirements.

The present invention provides for determination of lead polarity but does not require either the sensing of intrinsic heart signals or the generation of test signals. The present invention is based upon the premise that lead polarity can be determined using a measurement of lead impedance, also called electrode impedance. A lead impedance measurement value larger than a predetermined threshold level indicates either that no lead is present, that an electrode is broken or that the programming of the polarity mode is incorrect. A cardiac stimulation device, by measuring lead impedance during a bipolar pace, can determine if a bipolar lead is present. If the bipolar lead impedance measurement yields a value which is below the threshold impedance, a bipolar lead is connected to the stimulator. Otherwise, the stimulator may perform a unipolar lead impedance measurement to determine whether a viable unipolar lead is attached. Failure of the unipolar lead impedance test indicates either that no lead is attached to the stimulator or that the attached lead is broken.

The measurement of lead impedance is known in the art of cardiac pacemakers. For example, U.S. Pat. No. 4,448,196, entitled "Delta Modulator for Measuring Voltage Levels in a Heart Pacer", which issued on May 15, 1984 to D.K. Money et al., teaches a measurement circuit within a pacemaker which monitors lead impedance of a pacing lead by sensing the decrease in amplitude between the leading and trailing edges of a pacing pulse generated by the pacemaker as it performs its standard pacing function. The voltage of an output capacitor, the power source for tissue stimulation pulses, is sampled both before and after a stimulation pulse. The difference in voltage level between the two samples is caused by a partial discharge of the output capacitor during delivery of the stimulation pulse. This difference voltage value is used to determine the instantaneous lead impedance.

The lead polarity determination system of the present invention requires more than the usage of a lead impedance measurement to determine lead polarity to provide a viable stimulation device. The stimulator must continuously provide pacing support to a patient. If a unipolar lead is in place, the patient is not supported when a bipolar mode pacing pulse is delivered. Therefore, it is necessary to support unipolar pacing during each cardiac cycle of the lead polarity test. Thus the system of the present invention follows each bipolar pace with a unipolar backup pacing pulse shortly subsequent to the bipolar pace. In the preferred embodiment of the invention, the unipolar pace is delivered approximately 100 ms following the bipolar pulse. Note that if a bipolar lead is present, the bipolar pace supports the patient and no unipolar pace need be delivered.

Thus, it is an object of the present invention to test the polarity of a lead attached to an implanted stimulation device using a lead impedance measurement.

It is a further object of the present invention to automatically set the polarity mode of an implanted stimulation device to match a lead attached thereto on the basis of the results of a lead impedance measurement.

It is another object of the present invention to test the polarity of a lead attached to an implanted stimulation device using a lead impedance measurement which is functional via the sensing of a decrease in amplitude between the leading and trailing edges of a pacing pulse generated by the stimulator as it performs its standard pacing function.

It is an additional object of the present invention to test the polarity of a lead attached to an implanted stimulation device using a lead impedance measurement performed during the delivery of pacing pulses in which a bipolar pace measurement is followed by a unipolar backup pacing pulse shortly subsequent to the bipolar pace to assure the safety of a patient.

Further objects and advantages of the invention will become apparent as the following description proceeds.

SUMMARY OF THE INVENTION

Briefly stated, and in accordance with one embodiment of the present invention, a self-diagnostic lead polarity test system is provided within an implantable stimulating device. The implantable stimulating device is adapted to operate both in a bipolar mode and in a unipolar mode and is capable of receiving either a unipolar or a bipolar lead. Each electrode in the lead has an electrical impedance relative to the patient's body and the polarity test measures the electrode impedances to recognize whether the attached lead is a unipolar lead or a bipolar lead. The test system includes a stimulating pulse generator for generating and applying stimulating pulses of a predetermined pulse width to the stimulating lead. The system further includes a means operating during the generation of a stimulating pulse for acquiring a measurement relating to lead impedance. Also included is a means for storing externally-generated parameter values relating to lead impedance measurements. These parameter values identify whether the electrode type of the lead is unipolar or bipolar and indicate whether each of the electrodes is functional. The system further includes a controller comprising means for controlling the pulse generator to generate a stimulating pulse and take a lead impedance measurement while operating in the bipolar mode, and means for comparing the bipolar lead impedance measurement to the parameter values to determine the polarity and functionality of the electrodes.

If the lead electrode type is bipolar and the polar lead is functional, the controller operates the device in a bipolar mode. Otherwise, the controller operates the device to (i) change the device operating mode from bipolar to unipolar, (ii) time a predetermined interval following the generation of the bipolar mode stimulating pulse and (iii) control the pulse generator to generate a backup stimulating pulse while operating in the unipolar mode. When the system determines that the functional lead electrode type is other than bipolar, following the delivery of the unipolar backup pulse the controller may continue to operate the device in the unipolar mode.

The system further includes means for reporting whether the electrode type of the lead is unipolar or bipolar and whether each of the electrodes is functional. To do this the reporting means may include means for storing an indication of lead polarity, means for storing an indication of electrode functionality and means for storing lead impedance measurements. The reporting means may further comprise a telemetric communication means for transmitting diagnostic information to an external communicating device.

The polarity test system further includes a stimulating pulse power source for providing pulse power to the pulse generator at a predetermined voltage. The lead impedance measurement acquiring means preferably further comprises means for measuring a first voltage of the power source prior to delivery of a stimulating pulse, means for measuring a second voltage of the power source after delivery of the stimulating pulse, means for determining the difference between the first and second voltages and means for converting the voltage difference to a measurement of lead impedance. Preferably, the stimulating pulse power source is an output tank capacitor having a capacitance C, the stimulating pulse generator applies stimulating pulses for a predetermined pulse width T, and the lead impedance measurement R is derived in accordance with the following equation (1):

$$R = -T/(C*\ln(1-(V2-V1)/Vo)) \qquad (1)$$

wherein V1 is the first applied voltage and V2 is the second applied voltage Also, the means for comparing the bipolar lead impedance measurement to the parameter values preferably includes means for detecting a functional electrode when the lead impedance measurement is smaller than a prescribed impedance value.

BRIEF DESCRIPTION OF THE DRAWINGS

While the specification concludes with claims particularly pointing out and distinctly claiming the subject matter of the invention, it is believed that the invention will be better understood from the following description, taken in conjunction with the accompanying drawings, in which:

FIG. 6 is a table which characterizes the operations of switches in the circuits of FIGS. 4 and 5;

DETAILED DESCRIPTION OF THE INVENTION

Figure 1:
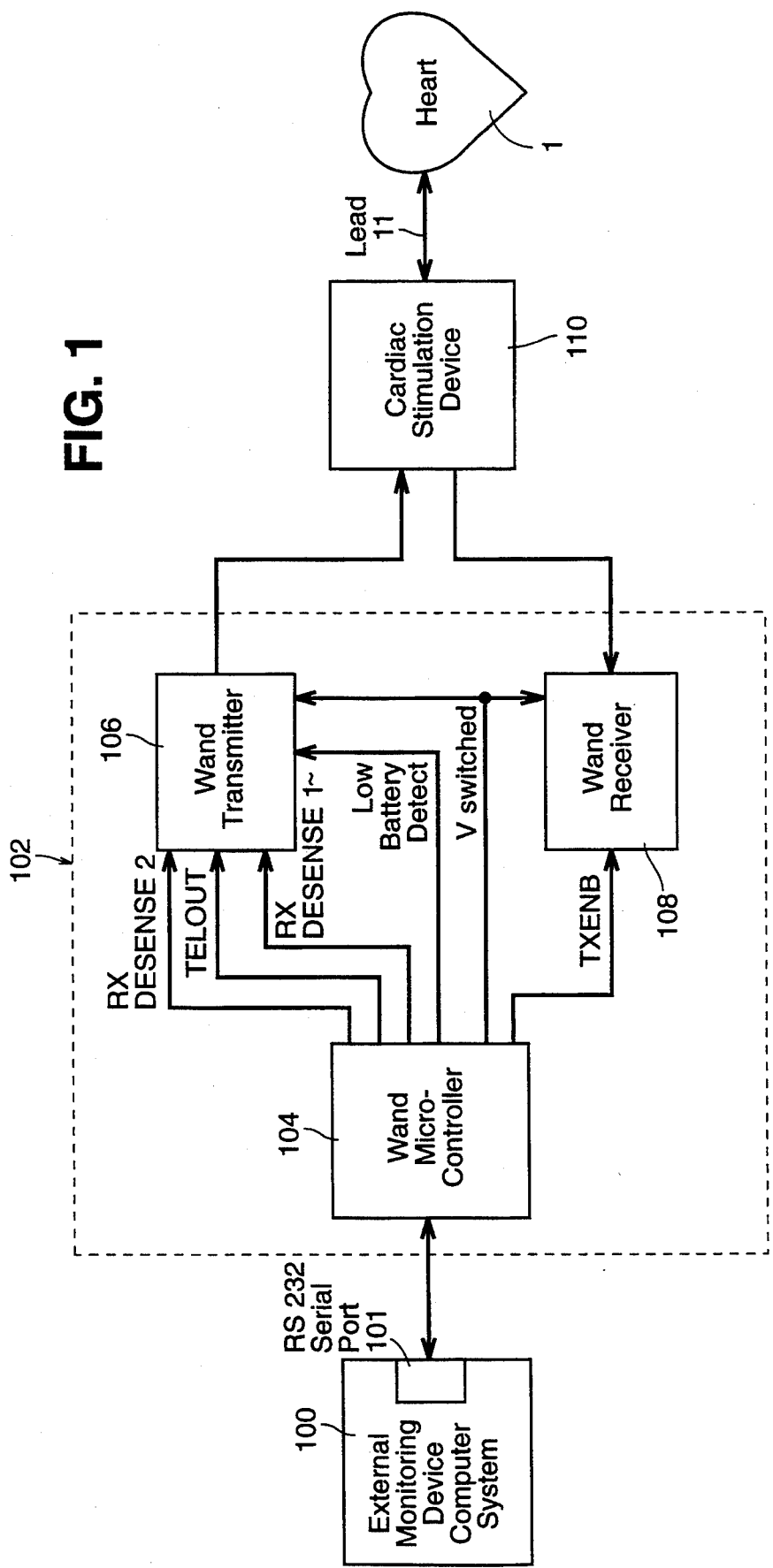
FIG. 1 is a high-level system block diagram showing the components of the present invention.

Referring to FIG. 1, an external monitoring device computer system 100 communicates with an implantable cardiac stimulation device 110 by means of a programming wand 102, which provides a telemetric communication link between the two. The cardiac stimulation device 110 employs a lead 11 to make an electrical connection to a heart 1 to stimulate the heart and to detect physiological signals from the heart.

The external monitoring device computer system 100 may be a standard personal computer (PC) system which executes programmer software known in the art of cardiac pacemakers, as well as new functions provided by the present invention.

The programming wand 102 of FIG. 1 provides a communications interface between the external monitoring device computer system 100 and the implantable cardiac stimulation device 110. Bidirectional communication between the programming wand 102 and the computer system 100 takes place using a high speed RS-232 serial port 101. A wand microcontroller 104, within the programming wand 102, receives data and control signal information from the computer system 100 and drives a wand transmitter 106 to send this information to cardiac stimulation device 110. This control information may be in the form of a request for the cardiac stimulation device 110 to transmit data such as self-diagnostic information and test results back to the computer system 100 for analysis and display. As the cardiac stimulation device 110 complies with this request for information, the programming wand 102 receives the telemetry signals sent by the cardiac stimulation device 110 in a wand receiver 108 and decodes and advances these signals to the external monitoring device computer system Physically, the programming wand 102 is a "mouse"-shaped housing (not shown) which contains circuitry for the wand microcontroller 104, the wand transmitter 106 and the wand receiver 108. The housing is connected by a coil cord (not shown) to a molded connector assembly (not shown) which connects to the RS-232 serial port 101 of the computer system 100. The connector assembly also contains a 9 volt battery (not shown), the power source for programming wand 102. Programming wand 102 circuitry includes functional circuits for wand microcontroller 104, wand transmitter 106 and wand receiver 108.

Figure 2:
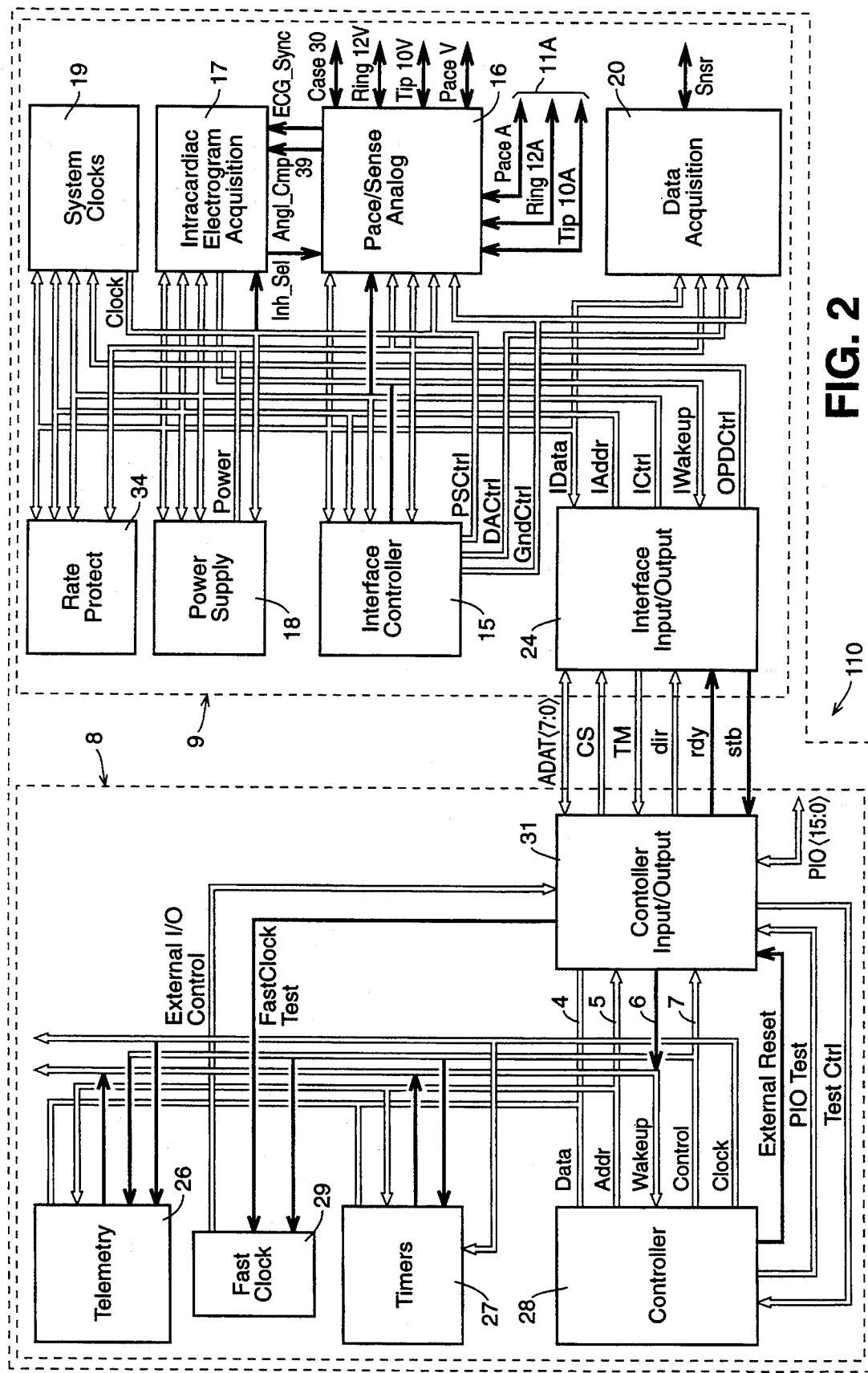
FIG. 2 is a high-level block schematic of an implantable cardiac stimulation device, a component of the present invention shown in FIG. 1.

Referring to FIG. 2, atrial tip and ring electrodes 10A and 12A, respectively, and ventricular tip and ring electrodes 10V and 12V, respectively, for respective atrial and ventricular channels, are those found in a conventional dual-chamber bipolar lead 11, the atrial channel position of which is shown at 11A in FIG. 2. Fundamental requirements for a cardiac stimulation device include the ability to generate and deliver, at selected intervals, electrical stimulation pulses of varying amplitudes and forms.

All logic for the implantable cardiac stimulation device 110 is under the control of a controller 28 (which may include a microprocessor), which controls all of the other blocks of FIG. 2. In the preferred embodiment of the invention, the controller 28 is a firmware-based microcontroller designed specifically for implantable applications. Controller 28 controls the acquisitions of a first applied voltage V1 and a second applied voltage V2. It then performs the lead impedance measurement R in accordance with the aforementioned equation (1):

$$R = -T/(C * \ln(1-(V2-V1)/Vo)) \tag{1}$$

wherein V1 is the first applied voltage and V2 is the second applied voltage The controller 28 fetches micro-coded instructions from a control store (not shown) ROM located internal to the controller, executes these instructions and sequences to the next instruction. The control store ROM contains executable control program instructions performed by the controller 28. The controller is inactive when no operations are pending, activates upon a "wakeup" command and executes other logic functions which are necessary in an algorithm-based implantable device. Logic blocks, such as a telemetry block 26, a timers 27 block, a pace/sense analog circuit 16, an interface controller 15 and an intracardiac electrogram acquisition circuit 17, generate wakeup commands which activate operations of the controller 28. In particular, the controller 28 may, through command signals to the interface controller 15, the pace/sense analog circuit 16 and a data acquisition circuit 20, determine the amplitude and shape of stimulating pulses, set the timing of pulse delivery and generate diagnostic test measurements.

Input signals to the controller 28 are a system reset signal, a 32 kHz clock signal, four wakeup lines from external subsystems and various execution clock signals. Output signals which are provided by the controller 28 to other subsystems are a chipwide reset signal, various clock subharmonic signals, and signals on digital data lines 4, address lines 5, and control lines 7.

Telemetry block 26 is a conventional communications circuit in modern implanted cardiac stimulation devices, such as pacemakers, defibrillators and antitachycardia pacemakers. By means of an antenna (not shown), the telemetry block 26 allows for bidirectional communication of information between an external (not implanted) programming device, such as the external monitoring device computer system 100 (FIG. 1), and the implantable cardiac stimulation device 110. Communication permits both an adjustment of the data acquisition parameters from the external programmer and transmission of information from the implanted device to the external device. The information transmitted from the implanted cardiac stimulation device 110 to the external programmer may include data and information representative of self-diagnostic measurement and test results. Present-day sophisticated telemetry circuits allow for the interrogation of stored diagnostic data and the derivation of real-time operational data.

Referring again to FIG. 2, the implantable cardiac stimulation device 110 uses timers 27 to measure various time intervals and provide timing control for circuit operations, physiological stimulation or activating or measuring real time events. The timers block 27 includes circuits to provide three independent interval timers—timer 0, timer 1 and timer 2 (not shown). The controller 28 writes timing initialization and duration information to timers 27. The timers 27 respond by generating wake-up signals T0, T1 and T2 (not shown), via wakeup lines 6, to the controller 28 after respective time intervals for timer 0, timer 1 or timer 2 expire. The controller 28 determines the duration of these time intervals by writing initialization and duration codes to control registers (not shown) within the timers 27. Timer 0 may be individually initialized to specify a timing resolution of 30 $\mu$s, 1 ms, 4 ms or 8 ms. The two remaining interval timers, timer 1 and timer 2, each may be individually initialized to specify a timing resolution of 1 ms, 4 ms or 8 ms. The controller employs timer wake-ups to govern the timing of cardiac cycles as well as to time short-term intervals for miscellaneous operations. The controller 28 may use timer wake-up signals to control a real-time clock function that determines the length of time since manufacture of the device and initiates long-term housekeeping functions such as self-diagnostic tests and measurements.

Controller input/output block 31 supports external input and output functions so that a processor subsystem 8, which includes the controller 28, the timers 27, the telemetry block 26 and a fast clock 29, can read and write data to and from external data lines to various source and destination subsystems, such as an interface subsystem 9. The controller input/output block 31 is an interface to external devices (not shown) that support read and write operations to control/status and data registers (not shown) in such external devices. Controller input/output block 31 provides for three modes of communication: memory-mapped input and output, a parallel input and output, and test modes.

An interface input/output block 24 provides an interface between the controller input/output block 31 of the processor subsystem 8 and interface subsystem 9, which includes the interface controller 15, the pace/sense analog circuit 16, the data acquisition circuit 20, the intracardiac electrogram acquisition circuit 17, a rate protection circuit 34, system clocks 19 (which supply stable crystal-controlled clock signals for numerous timing functions within the processor 8 and the interface 9 subsystems) and a power supply 18 (which furnishes the energy needs of the processor 8 and interface 9 subsystems). The interface input/output block 24 communicates with the controller input/output block 31 over an 8-bit bus ADAT<7:0>, which is multiplexed to communicate address and data information, and three control signals rdy, stb and dir to demultiplex and latch the address signals and provide direction control for data transmission. The controller input/output block 31 provides data and address lines ADAT<7:0> to the interface input/output block 24 and governs the operation of interface control signal lines, including data direction dir, ready rdy and strobe stb signal lines. The interface between the controller input/output block 31 and the interface input/output block 24 also includes chip select lines CS, allowing interfacing of multiple interface subsystems 9 with a single processor subsystem 8 and test mode lines TM, allowing testing of interface subsystem 8.

The interface input/output block 24 provides wakeup control signals on the bus ADAT<7:0> to the controller input/output block 31 to activate wakeup processing within the controller 28. The interface input/output block 24 controls wakeup lines, which are internal to the interface subsystem 9 and separate from wakeup lines within processor subsystem 8.

The interface input/output block 24 generates wakeup signals arising from various circuits within the interface subsystem 9. The interface input/output block 24 includes memory-mapped registers (not shown) for processing wakeups. These registers are accessed by the controller 28 via the data bus ADAT<7:0>. These registers allow the controller 28 to control wakeups generated by the interface subsystem 9 in a manner similar to that which the controller 28 uses to control processor subsystem 8 wakeups. The controller 28 regulates the operation of the interface wakeups using read and write operations to the interface wakeup registers over the bus ADAT<7:0>. The controller 28 may read an interface wakeup flag set register (not shown) to determine whether a particular interface wakeup has occurred and write to this register to force a wakeup to occur without regard to the state of the operations which normally activate such a wakeup. The controller 28 may write to an interface wakeup flag reset register (not shown) to clear an interface wakeup flag (not shown). The controller 28 may write to an interface wakeup mask register (not shown) to prevent interface operations which might activate a wakeup. An interface priority encoder circuit (not shown) within the interface input/output block 24, responds to an interface wakeup signal IWakeup by identifying the signal causing the interface wakeup and encoding this identity for reading by the controller 28 over bus ADAT<7:0>.

The interface controller 15, upon receiving commands from the controller 28 via the interface input/output block 24, generates timed sequences of latched control signals to control the operations of the data acquisition circuit 20, the pace/sense analog circuit 16 and the power supply 18. The interface controller 15 starts each sequence, as designated and initiated by the controller 28, and provides a wakeup signal to the controller 28 when the sequence is finished.

The interface controller 15 communicates to other circuits within the interface subsystem 9 via subsystem-wide data, address and control buses IData, IAddr and ICtrl, respectively. Timing signals are provided for the interface subsystem 9 on 16 kHz and 131 kHz clock lines (not shown). The interface controller 15 also sets latched control signals for various interface subsystem circuits. The state of all control signals at one time, in combination with control information for the interface controller 15 itself, is called an image.

Under the direction of the controller 28, via signals through the interface controller 15, the data acquisition circuit 20 performs sensor measurements, using line Snsr. In addition, the data acquisition circuit 20 sets the output voltage prior to the generation of any stimulation pulse.

Figure 5:
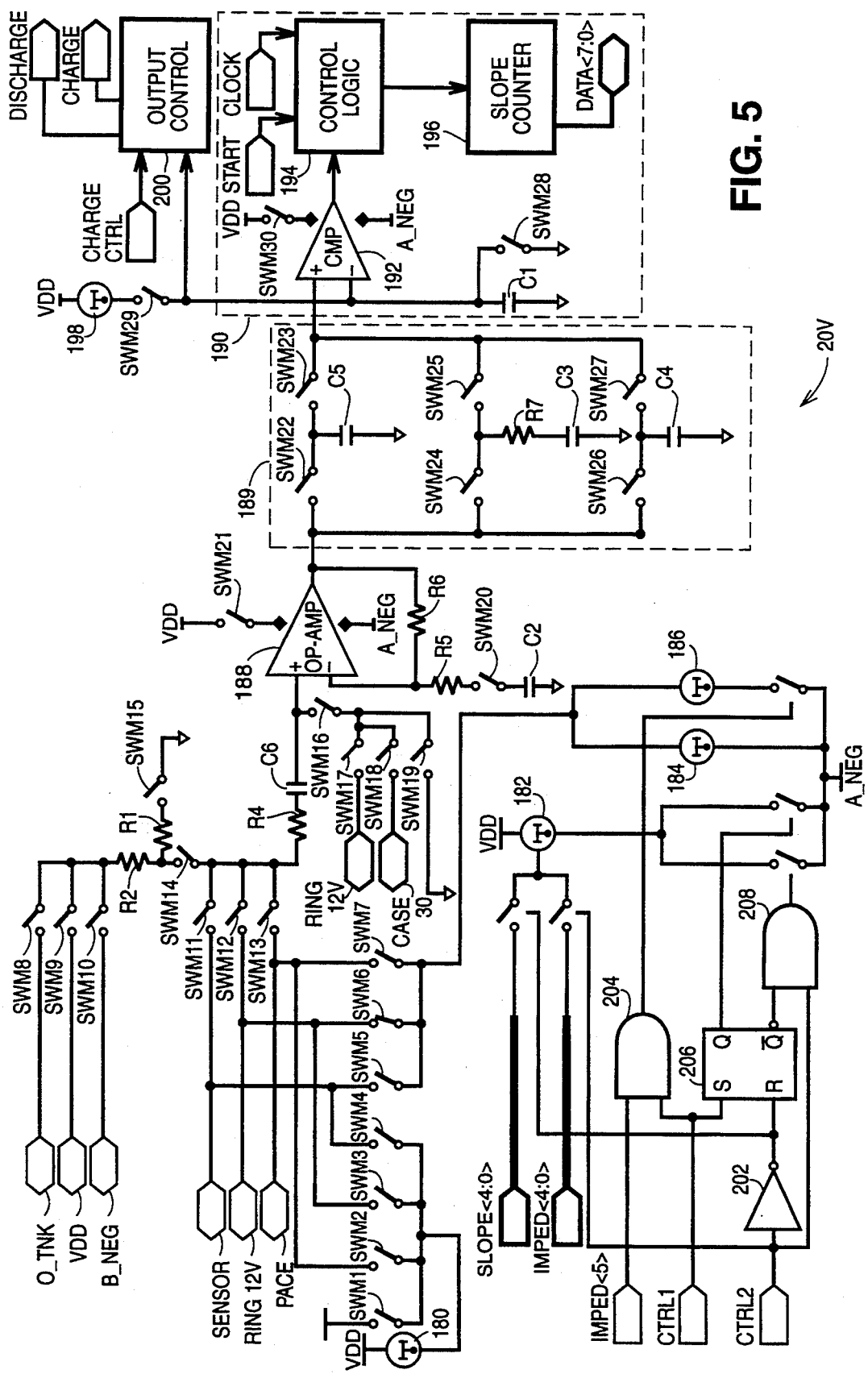
FIG. 5 depicts an illustrative embodiment of circuitry that is included in each of an atrial channel and a ventricular channel of a data acquisition block in FIG. 2.

The controller 28 directly writes calibration codes to memory-mapped registers (not shown) within the data acquisition circuit 20 to adjust measurements to reference measurement signal levels. In general, the controller 28 activates a measurement, or other operation, by writing a measurement-identifying command to the interface controller 15. In turn, the interface controller 15 carries out the measurement by generating signals which act on the data acquisition circuit 20. There are two types of measurements—sensor and diagnostic self-test measurements. The data acquisition circuit 20 performs all measurements of either type by differential sampling. In a first step of the differential sampling procedure, the data acquisition circuit 20 sets switches to sample a particular predetermined reference signal then stores the reference sample value on a first capacitor (C6 of FIG. 5). All measurements are performed by measuring the voltage which is generated across a sensor resistance (R4 of FIG. 5), which is generated by an injected constant-current source. Next, the data acquisition circuit 20 sets switches to sample a predetermined test signal, subtracts the reference sample value from the test sample value, and stores the test sample value on a second capacitor (one of capacitors C3, C4 or C5 of FIG. 5). The data acquisition circuit 20 may attenuate either or both the reference signal and the test signal prior to sampling. The data acquisition circuit 20 then places the sample value in a digital form by performing slope conversion on the signal stored on the second capacitor. The slope counter 196 of FIG. 5 is a counter within the data acquisition circuit 20 of FIG. 2, which times the interval required to charge a third capacitor (not shown) from 0 V to the voltage on the second capacitor (the differential test voltage) using a known current source. Following the completion of a measurement, the controller 28 may read the result of the measurement operation from a memory-mapped 10-bit measurement result register (not shown) within the data acquisition circuit 20 of FIG. 2. The result in the measurement result register is communicated from the data acquisition circuit 20 to the controller 28 via the IData bus in interface subsystem 9, bus ADAT<7:0> and the Data bus 4 in processor subsystem 8.

The apparatus and method of the present invention provides a cardiac stimulation device 110 that has the capability of performing self-diagnostic testing of lead polarity. Either a unipolar or a bipolar lead may be attached to the stimulation device 110, which may operate in either a bipolar mode or a unipolar mode with respect to pacing and sensing. The lead polarity test requires lead impedances to be measured in order to recognize whether the lead is a unipolar lead or a bipolar lead. To perform the lead polarity test, the stimulation device 110 includes circuits, which are generally contained within the pace/sense analog circuit 16, for generating stimulating pulses of a predetermined pulse width (determined by the controller 28). Furthermore, the lead polarity test requires circuits for acquiring a measurement relating to lead impedance, which circuits operate during the generation of a stimulating pulse. These circuits are generally contained in the data acquisition block 20. Also included in device 110 is a means for storing externally-generated parameter values relating to lead impedance measurements (not shown), which resides in RAM memory within the controller 28. These parameter values identify whether the electrode type of the lead is unipolar or bipolar and indicate whether such electrode is functional.

Figure 3:
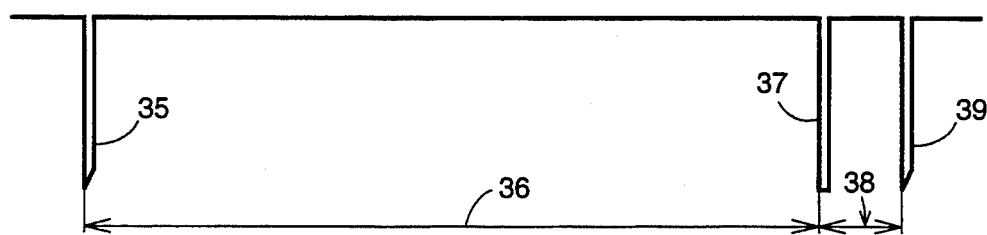
FIG. 3 depicts a time waveform which illustrates a method of providing combined pacing pulses and lead impedance test measurements in accordance with the present invention.

The measurement system further includes means for controlling the pulse generation circuits (not shown), within the pace/sense analog block 16 and the data acquisition block 20, to generate a stimulating pulse and to make a lead impedance measurement while operating in the bipolar mode. A bipolar stimulating pulse 37 is illustrated in the time waveform of FIG. 3, which depicts the manner in which combined pacing pulses and lead impedance measurement pulses are provided in accordance with the present invention. After making the lead impedance measurement, the controller 28 then utilizes a means (not shown) for comparing the bipolar lead impedance measurement to the stored parameter values to determine the polarity and functionality of the electrodes. A threshold value of these lead impedance parameters is generally in the range of from about 1000 ohms to about 3000 ohms with a preferred impedance of approximately 2000 ohms. Measured impedances smaller than this threshold value indicate the presence and functionality of an electrode. If the lead electrode type is bipolar and the bipolar lead is functional, the controller 28 operates the device in a bipolar mode. Otherwise, as shown in the time waveform illustrated in FIG. 3, the controller 28 operates the device to (i) change the device operating mode from bipolar to unipolar, (ii) time a predetermined interval 38 following the generation of the bipolar mode stimulating pulse 37 and (iii) control the pulse generator to generate a backup stimulating pulse 39 while operating in the unipolar mode. The predetermined time interval 38 is generally in the range of from about 30 ms to about 150 ms and has a preferred interval of approximately 100 ms. When the controller 28 determines that the functional lead electrode type is other than bipolar, following the delivery of the unipolar backup pulse 39 the controller may continue to operate the device in the unipolar mode.

The device 110 further includes means, such as the telemetry block 26, for reporting whether the electrode type of the lead is unipolar or bipolar and whether each of the electrodes is functional. RAM memory within the controller 28 may provide for storing lead polarity and electrode functionality information, as well as lead impedance measurements. The stimulation device 110 may also perform a unipolar measurement pacing pulse 35 either before or after the bipolar measurement pacing pulse 37 to determine whether any lead is attached to the device 110 and whether an attached lead is functional. The unipolar measurement pacing pulse 35 is delivered in a cardiac cycle that is different from that in which the bipolar measurement pulse 37 is delivered. (This means the unipolar measurement pulse 35 precedes or follows the bipolar measurement pulse 37 by at least one pace interval 36).

In the preferred embodiment of the invention, the pace/sense analog block 16 includes two circuits—one for an atrial channel and one for a ventricular channel. The circuit depicted in FIG. 4 corresponds to a pace/-sense analog ventricular channel 16V. The pace/sense analog atrial channel 16A is identical to channel 16V and therefore need not be further discussed herein. The pace/sense analog ventricular channel 16V includes twenty-one switches labelled SW1 through SW21. Depending on the mode of operation in which the circuit 16V is being operated at any given time, as determined by the controller 28, some of the switches are open and others are closed. FIG. 6 depicts a table that describes those switches SW1 through SW21 which are open and closed in each mode of operation. In addition FIG. 6 illustrates switch settings for switches SWM8, SWM14, SWM15, SWM16, SWM21, SWM22, SWM23, SWM28 and SWM30, which are used within the data acquisition circuit 20, shown in FIG. 5, to control a lead impedance measurement. It is to be understood that all of the switches are active circuits on an integrated circuit chip. FIG. 6 is a table which characterizes the operations of the switches of the pacing and sensing circuit 25 of FIG. 4 and the measurement circuit of FIG. 5. Represented switch conditions are described in the discussion of equivalent circuits in FIGS. 7, 8A, 8B, 9, 10, 11, 12, 13, 14, 15 and 16. The cardiac stimulation device 110 performs a procedure for measuring lead impedance during a pacing pulse. This procedure requires generation of a pacing pulse and is called "pulse generation and lead impedance measurement". Each line of the table describes switch settings for an operation of this procedure.

Figure 4:
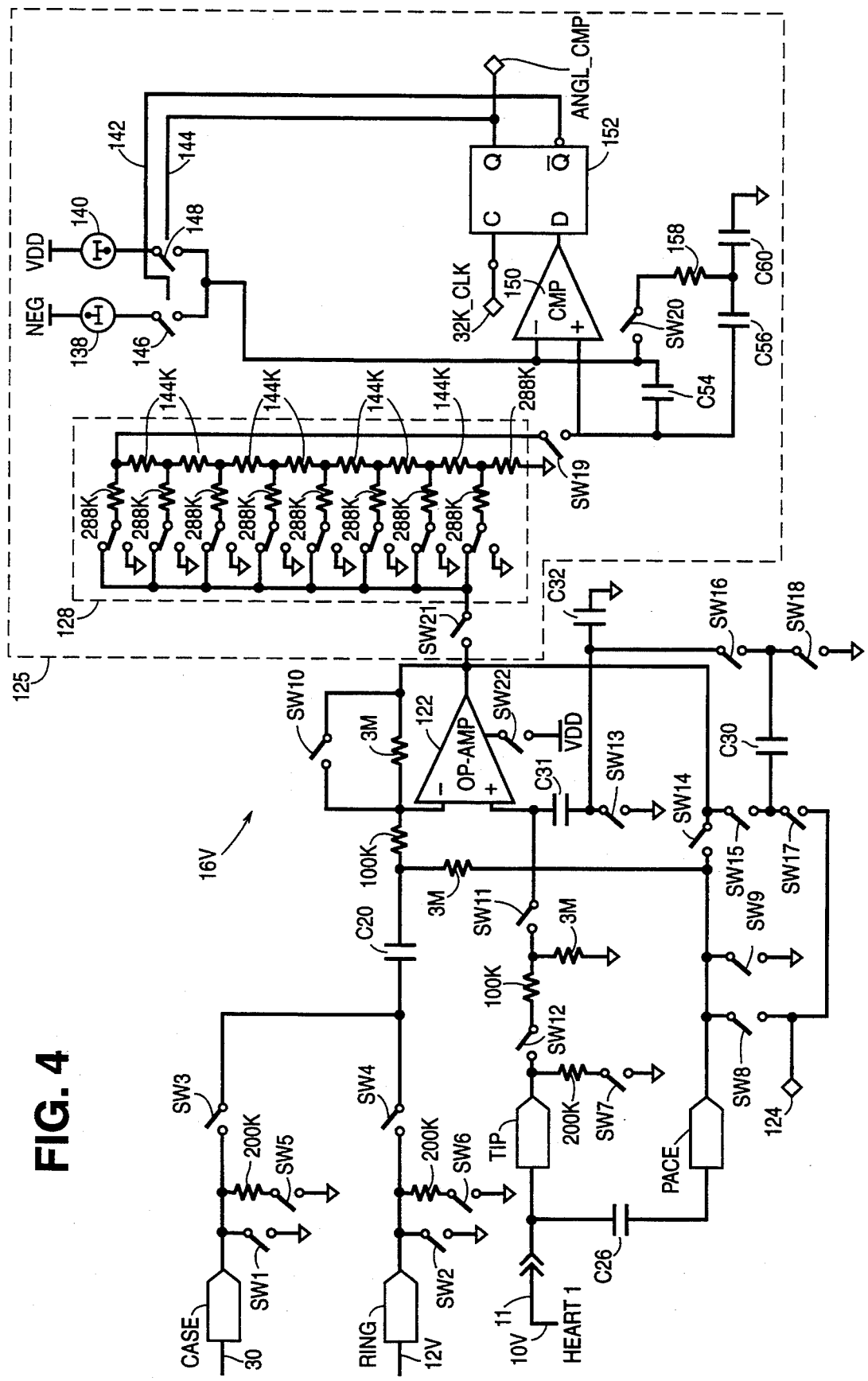
FIG. 4 depicts an illustrative embodiment of circuitry that is included in each of an atrial channel and a ventricular channel of a pace/sense analog block in FIG. 2.

Referring to FIG. 4, pin TIP and pin PACE are connected to the tip electrode 10V via lead 11, the PACE pin being connected through an external capacitor C26 (of, e.g., 7.5 uF). The tip electrode 10V provides a negative stimulus to the heart 1 and also permits sensing of cardiac signals by means of a connection to an amplifier 122 when switches SW11 and SW12 are closed. Two additional pins are provided in this circuit, labelled CASE and RING. If the cardiac stimulation device 110 employs a bipolar lead 11, the indifferent electrode can be either the ring electrode 12V or the case 30. If a unipolar electrode is used, then the indifferent electrode must be the case 30. The pin labelled CASE is electrically connected to the case 30. The pin labelled RING is connected to the ring electrode 12V only if a bipolar lead is employed. If a bipolar lead is used, the positions of switches SW1 through SW4 select between the two possible indifferent electrodes (ring 12V or case 10).

The switches SW5, SW6 and SW7 are opened or closed together and control the connection of the two possible anodes (case 30 or ring electrode 12V) and the stimulating cathode (tip electrode 10V) to the reference ground. During cardiac signal processing (sensing), all three of these switches are closed, as are switches SW19 and SW20. The latter two switches are closed so that the circuit forms a delta modulator and bandpass filter 125 through the operations of a comparator 150 and a DC flip-flop 152. The three former switches (SW5-SW7) are closed to connect each of the three inputs through a 200 K resistor to reference ground. At all other times, according to the table of FIG. 6, the five switches are open. Switches SW19 and SW20 are held open so that the delta modulator and bandpass filter 125 functions as a sample-and-hold circuit. Switches SW5, SW6 and SW7 are similarly held open because it is not desired that current flow through the case 30, ring 12V or tip 10V and the respectively connected 200 K resistors to reference ground. During the various phases of switch settings when the pace/sense analog circuit 16V is involved in pacing, and even when the cardiac stimulation device 110 is performing various sensor measurements, current pulses are applied by the device 110 and it is undesirable for any of the current to be allowed to flow through the 200 K resistors. The provision of separate switches for the case electrode 30 and ring electrode 12V inputs allows a dual chamber cardiac stimulation device 110 to be made, using an atrial channel duplicate of the pace/sense analog channel 16V of FIG. 4. This allows the different chambers to be paced in different modes—unipolar or bipolar.

A capacitor C20 (of, e.g., 0.1 uF) is a standard coupling capacitor which is provided to block DC on the electrodes and to prevent the propagation of noise through the operational amplifier 122 from being amplified. Operational amplifier 122 has a gain of 30 when switch SW10 is open, this being the ratio of the feedback resistor (3M), between the output of the amplifier 122 and the minus input, to the input resistor (100 K) connected to the minus input. The operational amplifier 122 functions to equalize the two signals at its minus and plus inputs. However, in practice this is not possible to achieve, and some offset voltage across the plus and minus inputs of the operational amplifier 122 exists. This offset voltage is stored on the capacitors C20 and C26.

Capacitor C26 is a standard-type AC coupling capacitor for generating a pacing stimulus, which is powered by means of a potential at an output potential node 124. This potential may vary between 0 and 7.5 volts in the illustrative embodiment of the invention. The circuits from which the output potential is derived are not important for understanding of the present invention. The output potential magnitude may be set by an external programmer via operations of the telemetry circuit 26 shown in FIG. 2. Charge pump capacitor C30 (e.g., 10 pF) and ramp capacitors C31 (e.g., 20 pF) and C32 (e.g., 1.2 nF), under the control of the interface controller 15 of FIG. 2 via switches SW13, SW14, SW15, SW16, SW17 and SW18, control the waveform shape of the pacing pulse.

Sensing of cardiac signals may be accomplished by connecting the output from the amplifier 122 to delta modulator and bandpass filter 125 via switch SW21. The first stage of the delta modulator and bandpass filter 125 is a resistor network 128, which comprises a standard R-2R ladder network with standard binary weightings. Resistor network 128S serves as an attenuator and controls sensitivity for heart signal sensing. An eight bit register (not shown) is set by the controller 28 to control the sensitivity via the position of switches in the ladder network. Delta modulator and bandpass filter 125, which is described in U.S. Pat. No. 4,692,719 entitled "Combined Pacemaker Delta Modulator and Bandpass Filter" to R.H. Whigham on Sep. 8, 1987, is comprised of the resistor network 128, comparator 150, capacitors C54 (e.g., 22 nF), C56 (e.g., 50 nF) and C60 (e.g., 50 nF) and a resistor 158. Delta modulation provides for conversion of a cardiac signal into a digital form for usage by the cardiac stimulation device 110. A Q output of the DC flip-flop 152, extended to node ANGL_CMP, is a two-level signal which is derived from the signal at the lead tip electrode 10V after attenuation by the ladder network 128. The signal from the ladder network 128 is applied to the plus input of the comparator 150. ANGL_CMP output signals follow the input signals from the lead 11 tip electrode 10V in the sense that the output represents a 1 when the input is increasing and represents a 0 when the input is decreasing.

The delta modulator 125 includes, in addition to the aforementioned resistor network 128, comparator 150 and DC flip-flop 152, two oppositely-poled current sources 138 and 140, respectively connected to the negative voltage supply MEG and the positive voltage supply VDD. The outputs of the DC flip-flop 152 control switches 146 and 148 via lines 142 and 144, respectively. When switch 148 is closed, current flows to the negative voltage supply MEG through constant current source 138 and when the switch 148 is closed, current flows from positive voltage supply VDD through constant current source 140.

In the preferred embodiment of the invention, the data acquisition block 20 (FIG. 2) includes two circuits—one for an atrial channel and one for a ventricular channel. The circuit depicted in FIG. 5 corresponds to a data acquisition ventricular channel 20V. The data acquisition atrial channel 20A may be identical, although some inputs (for example SENSOR) may not be included. The data acquisition atrial channel 20A therefore need not be further discussed. The data acquisition ventricular channel 20V includes thirty switches labelled SWM1 through SWM30. Depending on the mode of operation in which the circuit 20V is being operated, as determined by the controller 28, some of the switches are open and others are closed. The table depicted in FIG. 6 describes those switches which are opened and closed in each mode of operation employed during a lead impedance measurement, the relevant measurement for the present invention. It is to be understood that all of the switches are active circuits on an integrated circuit chip. The data acquisition circuit 20V may perform numerous sensor and self-diagnostic measurements, each of which is performed by the timed setting and resetting of particular switches. Only those switches which are operated during a lead impedance measurement and only those components of the circuit which are activated by those switches, will be discussed in detail.

The data acquisition circuit 20V executes all measurements by differential sampling in a multiple step procedure whereby a first sample is measured and the resulting potential stored on a capacitor C6 (e.g., 50 pF). For the data acquisition ventricular channel 20A, this capacitor C6 may have a smaller capacitance. In a subsequent step, the data acquisition circuit 20V measures a second sample, subtracts the potential stored on the capacitor C6 from the result and stores the difference potential on a selected capacitor C3, C4 or C5 (e.g., 1.0 nF, 25 pF or 25 pF). This potential is converted to digital form by means of a slope converter 190 which consists of a comparator 192, a control logic block 194 and a slope counter 196. The step size of the slope converter 190 is determined by a digital programming control register signal SLOPE<4:0> from the controller 28. SLOPE<4:0> sets the magnitude of current sources 182, 184 and 186 to charge a slope capacitor C1 (e.g., 4.7 uF).

The data acquisition ventricular channel circuit 20V provides for the measurement of multiple parameters. These parameters include physiological sensor sampling and self-test measurements regarding the diagnostic function of the cardiac stimulation device 110. The parameter of interest in the present invention is a lead impedance measurement. The data acquisition ventricular channel 20V has input connections to multiple signal sources to allow for measurement of these multiple parameters. The particular measurement which is performed is selected by means of multiple switches. The lead impedance measurement employed in the cardiac stimulation device 110 of the present invention is activated by setting switch SWM8. Other measurements are actuated when switches SWM9, SWM10, SWM11, SWM12 or SWM13 are closed. The switch settings for the various suboperations of a particular measurement determine how a measurement is performed. The table of FIG. 6 depicts the switch settings for the lead impedance measurement.

Some measurements are performed by measuring the voltage generated by a constant current source. The lead impedance measurement of interest in the present invention does not function in this manner. Referring to FIG. 5, constant current source 180 generates a current of programmable magnitude for such lead impedance measurements. The controller 28 of FIG. 2 provides programmable control via a register (not shown), which delivers signals to the data acquisition circuit 20V via digital signal level line IMPED<4:0> and control line IMPED<5>. Switches SWM1, SWM2, SWM3, SWM4, SWM5, SWM6 and SWM7 are closed for measurements which test the voltage resulting from a constant applied current. When these switches are closed, the circuit comprising AND gates 204 and 208, a NOT gate 202 and an RS flip-flop 206 is activated. Since this circuit is not in operation for the lead impedance measurement of importance in the present invention, it is not discussed.

The data acquisition circuit 20V is capable of connecting various nodes within the cardiac stimulation device 110 for the purpose of making a plurality of measurements in a versatile manner. Thus, the data acquisition ventricular channel 20V may connect a selected input signal to the ring electrode 12V through a RING pin, to the case 30 through a CASE pin or to reference ground by setting switches SWM16, SWM17, SWM18 and SWM19. If such a connection is made, the completed circuit traverses resistors R2 (e.g., 300 K) and R4 (e.g., 33 K) and the capacitor C6, while closed switch SWM15 connects the node between R2 and R4 to ground through a resistor R1 (e.g., 100 K). For example, these switches may be configured to apply a selected current source to an electrode or to store a selected signal potential on the capacitor C6.

In accordance with the configuration of the aforementioned switches, an input signal or a potential stored on the capacitor C6 may be applied to the operational amplifier 188, which is activated when the switch SWM21 is closed and the positive voltage source VDD is applied to the amplifier 188. The operational amplifier 188 may be configured as a unity gain buffer for diagnostic self-test measurements or it may provide gain and high-pass filtering for physiologic sensor sampling functions when switch SWM20 is closed, thereby including a resistor R5 (e.g., 27 K) and a capacitor C2 (e.g., 56 pF)

in the operational amplifier 188 circuit. Resistor R6 (e.g., 270 K) connects operational amplifier 188 output to its minus input.

Output from the operational amplifier 188 is applied to a sample-and-hold circuit 189. Switches SWM22 and SWM23 are operated to store the result of the differential sampling on the measurement capacitor C5. Physiological sensor samples, the .measurement of which are not relevant to the present invention and not further discussed, are acquired on capacitors C3 and C4 through the operations of switches SWM24, SWM25, SWM26 and SWM27 and resistor R7. Output of the sample-and-hold circuit 189 is applied to the slope converter 190, which is activated by setting switch SWM30 to power the comparator 192.

The data acquisition ventricular channel 20V also includes circuits for setting the pacing output voltage and storing this voltage on a capacitor (not shown). These circuits include an activating switch SWM29, a current source 298 and an output control circuit 200. These circuits are not important with respect to the present invention and are not discussed further.

In general, when the cardiac stimulation device 110 is not delivering a pacing pulse, it is sensing intrinsic cardiac signals. This operation is termed "sensing" and is accomplished by the cardiac stimulation device 110 when the settings of the switches within the pace/sense analog channel 16V shown in FIG. 4 are set in accordance with the "sensing" row shown in the table of FIG. 6 to provide the equivalent circuit shown in FIG. 7. Note that the same switch settings are provided for activating the atrial pace/sense analog channel 16A for measuring the impedance of the atrial electrode. Referring to FIG. 6, during sensing the switches SW1 and SW2 are open and the switches SW5 and SW6 are closed. If bipolar sensing is selected, then switch SW4 is closed and switch SW3 is open, thereby designating the ring electrode 12V as the anode for sensing. If unipolar sensing is selected, then switch SW4 is open and switch SW3 is closed, selecting the case electrode 30 as the anode for pacing. Thus, as shown in FIG. 4, the effective anode is connected through a 200 K resistor to reference ground (via SW5 and SW6) and is also connected to the capacitor C20 (via SW3 or SW4). These 200 K resistors, as well as the 200 K resistor connecting the TIP pin to reference ground through switch SW7, are provided to hold the ring, case and tip electrodes within a few millivolts of ground potential.

Figure 7:
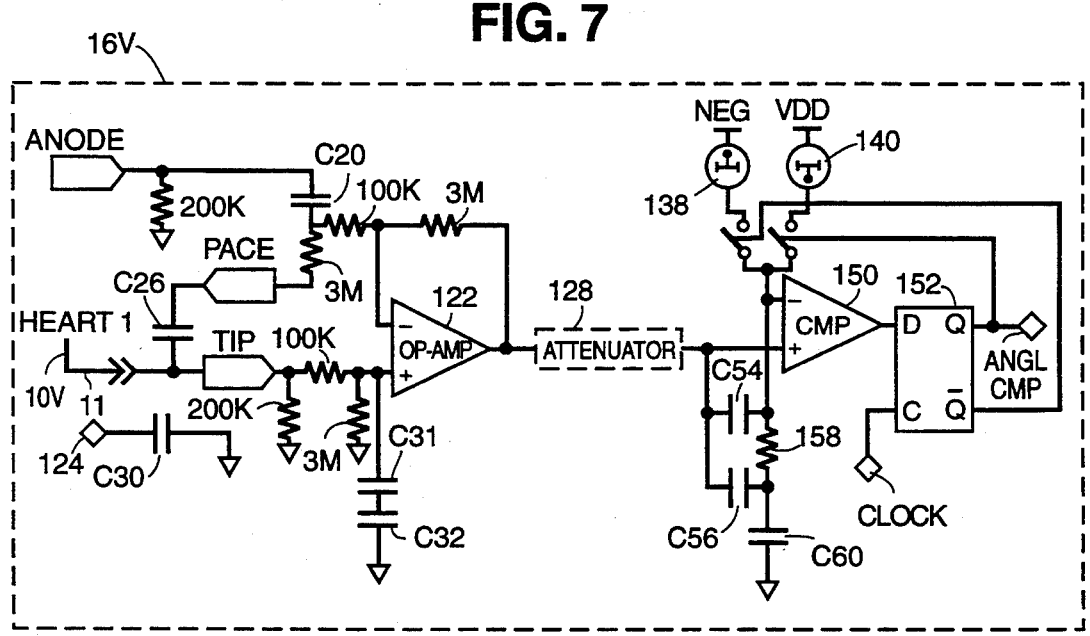
FIG. 7 depicts the status of components in the circuit of FIG. 4 when the switches in FIG. 4 are activated in accordance with the table of FIG. 6 during a "sensing" phase of operation.

.Referring to FIGS. 4, 6 and 7, together, during sensing the operational amplifier 122 is configured as a differential amplifier and has connections to its minus input which include an AC coupling capacitor C20, a 100 K input resistor and a 3M feedback resistor in a feedback path from the amplifier output, the latter resistor having open switch SW10 connected thereacross. This ratio of resistances provides a gain of 30 to the amplifier. The plus input to the operational amplifier 122 is provided with a signal from the TIP pin through closed switches SW11 and SW12 to allow cardiac signal sensing. This signal path includes a 100 K input resistor and a 3M resistor tied to ground. In addition, the heartbeat sensor circuit includes a 3M resistor, which is connected between the PACE pin and the capacitor C20, to maintain an offset voltage between the plus and minus inputs of the operational amplifier 122. Current driven by the offset voltage flows through the latter 3M resistor and through the capacitor C26 to charge the capacitor to the offset voltage magnitude.

During sensing, switch SW13 is closed to connect the series ramp capacitors C31 and C32 to reference ground. Switches SW17 and SW18 are closed so that the charge pump capacitor C30 is connected between reference ground and the output potential at node 124 to store the output voltage until a pacing pulse is delivered. Switch SW21 is closed to connect the output signal from the amplifier 122 to the attenuator 128, the first circuit element within the delta modulator and bandpass filter 125. The output from the attenuator 128 connects to the comparator 150 through closed switch SW19. The cardiac stimulation device 110 closes switch SW20 so that the delta modulator and bandpass filter 125 samples the cardiac signal during the sensing phase.

Sensing does not require the interface controller 15 (of FIG. 2) to set any of the switches in the data acquisition circuit 20V (FIG.5). This circuit may be activated to perform other independent measurements during the sensing operation.

Figure 8A:
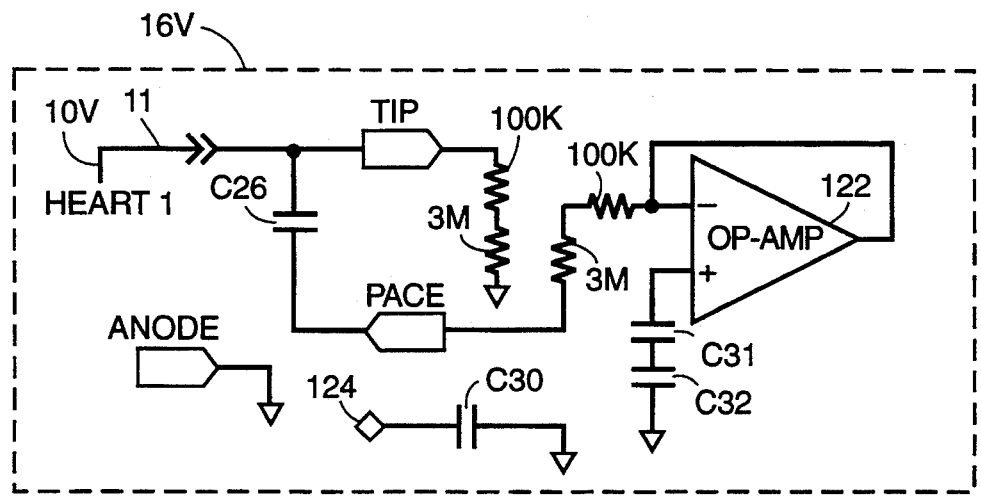
FIGS. 8A and 8B depict the status of components in the circuits of FIGS. 4 and 5, respectively, when the switches in FIGS. 4 and 5 are activated in accordance with the table of FIG. 6 during a "sample/disconnect tip" phase of operation.
Figure 8B:
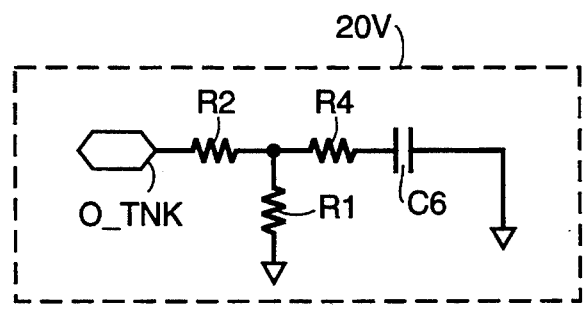

Referring again to FIG. 6 in conjunction with FIGS. 4, 5, 8A and 8B, the next operation in the lead impedance measurement is the "sample/disconnect tip" procedure, which disconnects the tip electrode 10V from the operational amplifier 122, grounds the effective anode and samples the output voltage. The activated circuits for the pace/sense channel circuit 16V and the data acquisition channel circuit 20V during the tip disconnect operation are shown in FIGS. 8A and 8B, respectively. Note that the same switch settings are provided for activating the atrial pace/sense analog channel 16A and the atrial data acquisition channel 20A for measuring the impedance of the atrial electrode. The switches within the pace/sense analog circuit 16V of FIG. 4 are set in accordance with the table of FIG. 6 for the "sample/disconnect tip" operation to create the equivalent circuit shown in FIG. 8A. If bipolar pacing is selected, then switch SW2 is closed and switch SW1 is open, specifying the ring electrode as the anode. If unipolar pacing is selected, then switch SW2 is open and switch SW1 is closed, selecting the case electrode as the anode and connecting the anode to ground while a pacing pulse is generated. Each of the switches SW3 and SW4, which would otherwise connect the case and ring electrodes to the operational amplifier 122, is open. Since the selected anode is connected to ground and the unselected anode is isolated from the operational amplifier 122 by open switches SW3 and SW4, switches SW5, SW6 and SW7 are held open because it is not necessary to connect these electrodes to reference ground through 200 K bypass resistors. Switch SW21 is open to disconnect the amplifier 122 from the delta modulator and bandpass filter 125 since the cardiac signal cannot be measured during a pacing pulse. Switches SW19 and SW20 are open to hold the charge on the bandpass filter capacitors C54, C56 and C60. During the sample/disconnect tip operation, the TIP pin is disconnected from the operational amplifier 122 by opening the switch SW11. The interface controller 15 (FIG. 2) connects the tip electrode 10V to reference ground through 100 K and 3M resistors in series by closing switch SW12 and opening switch SW7. Switch SW13 is opened to disconnect the ramp capacitor C32 from reference ground. The operational amplifier 122 is disconnected from the electrode inputs since switches SW3, SW4 and SW11 are open, and its output is fixed by the operation of switch SW10. Switch SW10 is closed, shunting the 3M feedback resistor, so that the output of the operational amplifier 122 is connected to its minus input. Switches SW17 and SW18 remain closed to continue charging the charge pump capacitor C30 to the output potential at node 124.

The cardiac stimulation device 110 executes a lead impedance measurement simultaneously with the generation of a pacing pulse by controlling switches of the data acquisition circuit 20. Referring to the ventricular data acquisition channel circuit 20V in FIG. 5 and the sample/disconnect switch settings for this circuit in the table of FIG. 6 the corresponding equivalent circuits within the data acquisition channel circuit 20V, are shown in FIG. 8B. At this time, the voltage on an output tank capacitor (not shown), output potential O_TNK, is sampled on the capacitor C6 prior to the delivery of a pacing pulse. This is accomplished by closing switches SWM8, SWM14, SWM15 and SWM16. One of the switches SWM17, SWM18 or SWM19 is always closed, depending on which electrode (ring, or case or neither) is configured to define reference ground. Switches SWM9 through SWM13 are open previous to this operation and remain open so that the output potential O_TNK is the only input signal applied to the circuit. Switch SWM16 was open previous to this operation and remains open so that the O_TNK input potential is not applied to either the ring electrode, the case or reference ground. The interface controller 15 controls the duration of the sample/disconnect tip operation so that it lasts a sufficient time to charge the capacitor C6, for example about 30 μs. The potential Vo stored on the capacitor C6 is set in accordance with equation (2):

$$VO = -O_{TNKb} * (R1/(R1+R2)) \quad (2)$$

where $O_{TNKb}$ is the output tank capacitor voltage before pacing.

Figure 9:
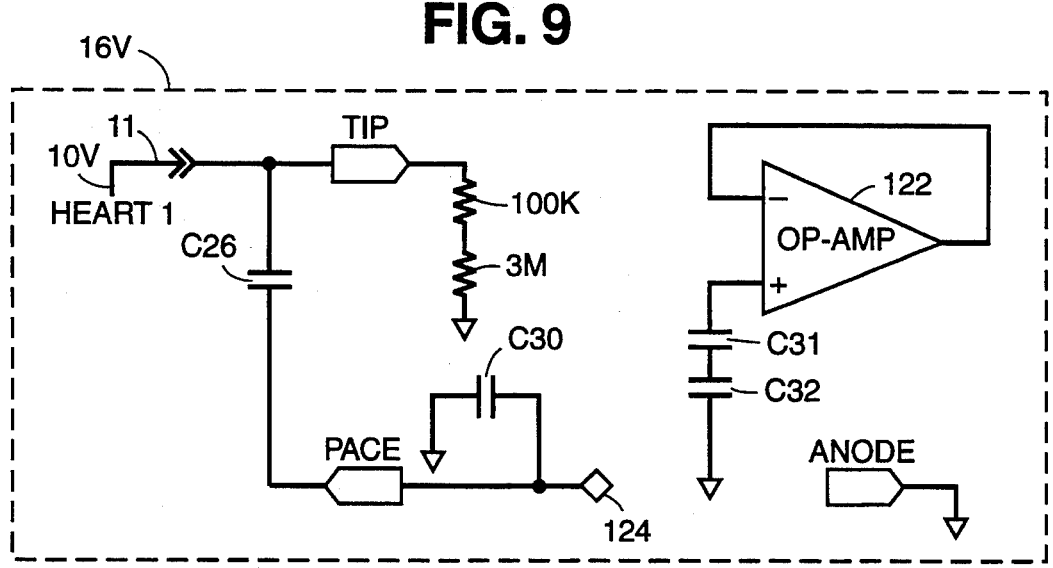
FIGS. 9–13 depict the status of components in the circuit of FIG. 4 when the switches in FIG. 4 are activated in accordance with the table of FIG. 6 during additional different phases of operation.
Figure 10:
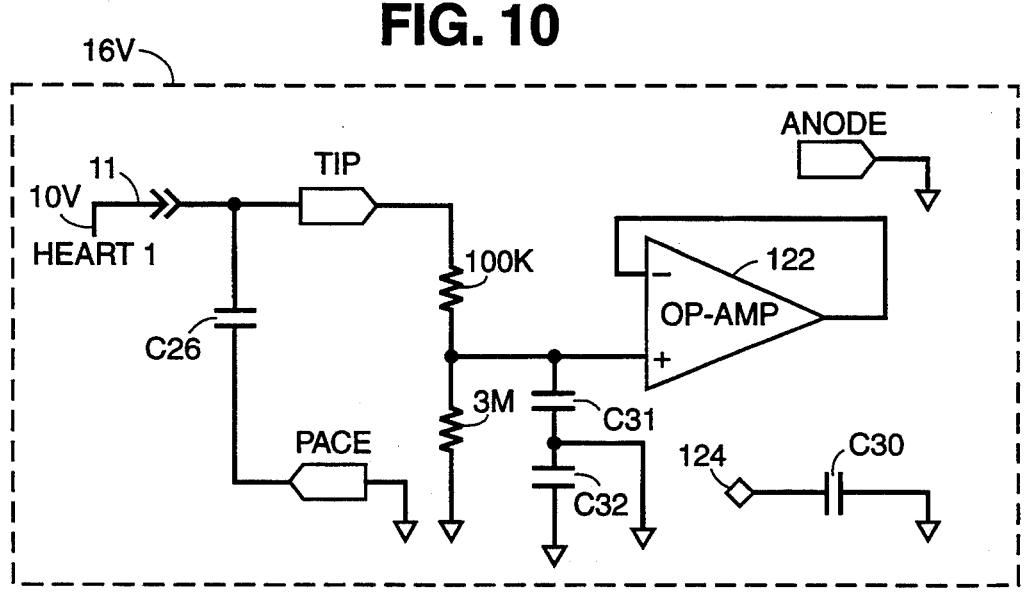

The active components of the pace/sense analog channel circuit 16V during the stimulus phase of FIG. 6 are shown in FIG. 9. During the stimulus phase, the PACE pin is connected to the output node 124. Referring to the "stimulus" row in the table of FIG. 6, in conjunction with FIGS. 4, 5 and 9, switch SW8 is changed from an open to a closed state to connect the charge pump capacitor C30 (FIG. 4), across which an output pacing potential has been developed, to the output capacitor C26. Switch SW14 remains open to continue to disconnect the output of operational amplifier 122 from tip electrode 10V. The charge pump capacitor C30 now discharges through capacitor C26 to generate a negative stimulus to the heart 1. During the stimulus phase, switches SWM8 and SWM16 within the data acquisition channel circuit 20V (FIG. 5) are open to store the sampled potential Vo on capacitor C6 while the pace/sense analog channel circuit 16V generates the remainder of the pacing pulse in a "passive post charge" phase, a "boost turn on" phase, an "active post charge" phase and a "boost turnoff" phase. During these phases, switches SWM14 and SWM15 of data acquisition channel circuit 20V remain closed. The duration of the stimulus pulse width is set by the controller 28 in the range of from approximately 30 μs to 2 ms.

Following the stimulus pulse, the pace/sense analog channel circuit 16V (FIG. 4) is controlled, according to the switch settings shown in FIG. 6, to passively discharge the output coupling capacitor C26 in a "passive post charge" operation, which lasts for about 14 ms. In this manner, the pace/sense analog circuit 16V provides for approximate balancing of the charge injected into the patient's heart tissue since the output coupling capacitor 026, which was charged by capacitor C30 during the stimulus pulse, now discharges back into the patient. In this connection, the PACE pin is connected to ground when the switch SW9 is closed. The TIP pin is reconnected to the positive input to the operational amplifier 122 at the closure of switch SW11 and the PACE pin is disconnected from the output node 124 and capacitor C30 by the opening of switch SW8 to terminate the stimulus delivery. The passive post charge operation hastens the dissipation of charges in body tissues following the delivery of the negative pacing stimulus.

Figure 11:
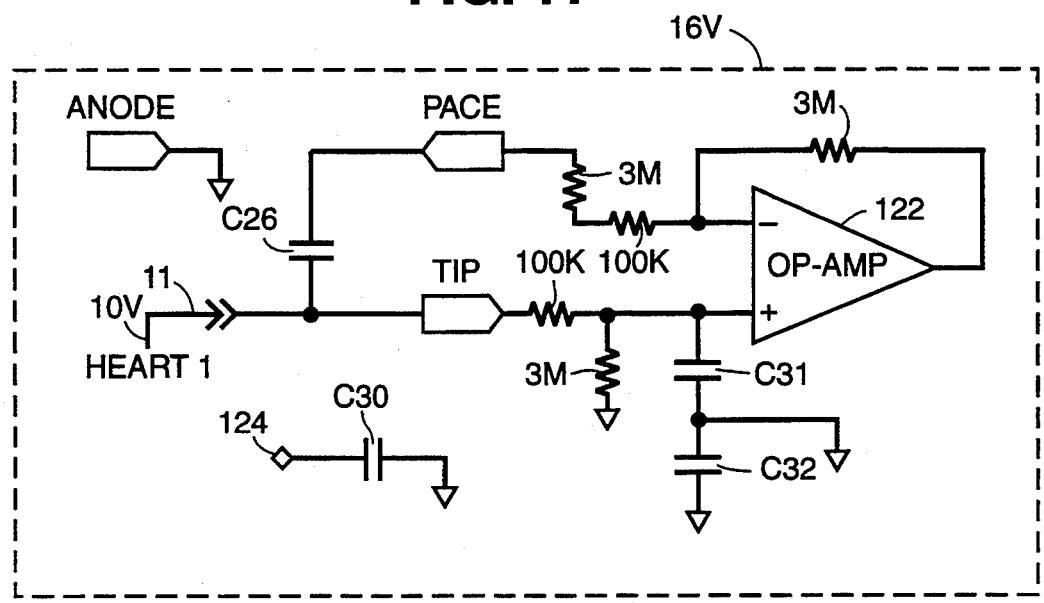

Referring now to the boost turn on operation illustrated by the circuit of FIG. 11, in conjunction with FIG. 4, a switch SW22 is closed to increase the output power capability of the operational amplifier 122 during a boost turn on time duration of about 300 μs between the passive and active post charge pulse phases. Switch SW9 is opened to disconnect the PACE pin from ground and switch SW10 is opened to insert the 3M feedback resistor into the feedback loop from the output to the minus input of the operational amplifier 122.

Figure 12:
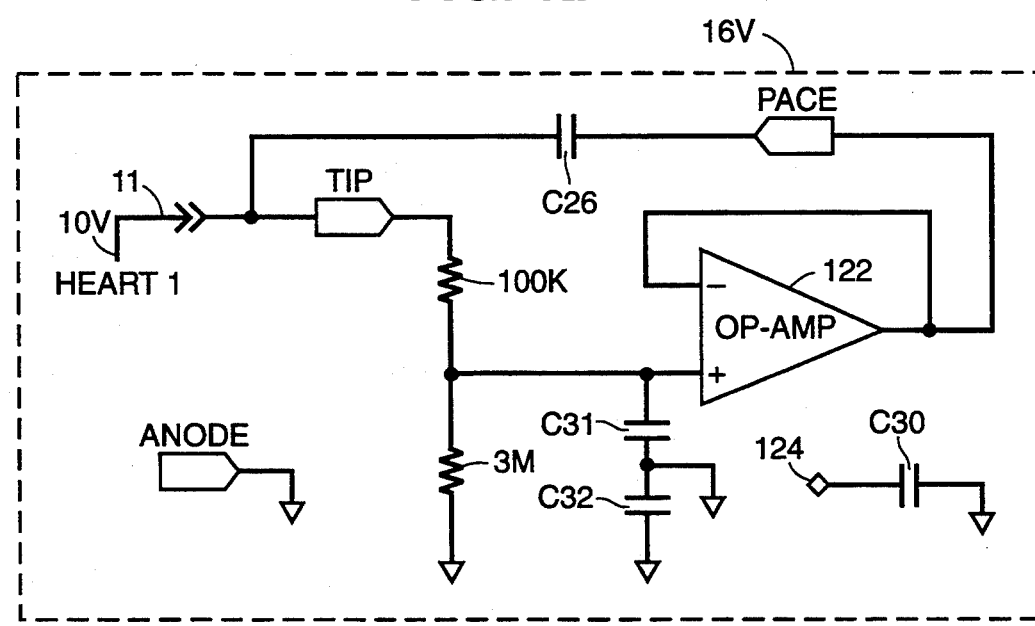

An "active post charge" operation, illustrated by the pace/sense analog channel circuit 16V of FIG. 12 and the switch settings of the active post charge row of FIG. 6, adds a small active post charge pulse of about 2 ms duration to finish the pacing sequence with a precise charge balance. This is done to prevent buildup of a residual charge on the coupling capacitor C26 to allow for sensing of physiological signals, such as impedance signals, using the pacing electrodes.

There is a part of the pace/sense analog circuit 16 called a protect cell (not shown), which forces a passive post charge operation even when an active post charge operation is requested. This occurs if the voltage across the capacitor C26 is greater than a predetermined threshold, which may occur when stimulator 110 is postcharging into a short circuit or a defibrillator pulse is generated by another device. The protect cell asserts a protect signal when it detects an excess voltage across the capacitor C26. A protect signal occurring during the active post charge phase of the stimulating pulse closes the switch SW9, thereby connecting the PACE pin to reference ground. Normally, a protect signal will not occur and the switch SW14, rather than switch SW9, will be closed during the active post charge phase, connecting the PACE pin to the output of the amplifier 122 so that the output of the amplifier 122 drives the tip electrode 10V, as shown in the effective circuit of FIG. 12.

Figure 13:
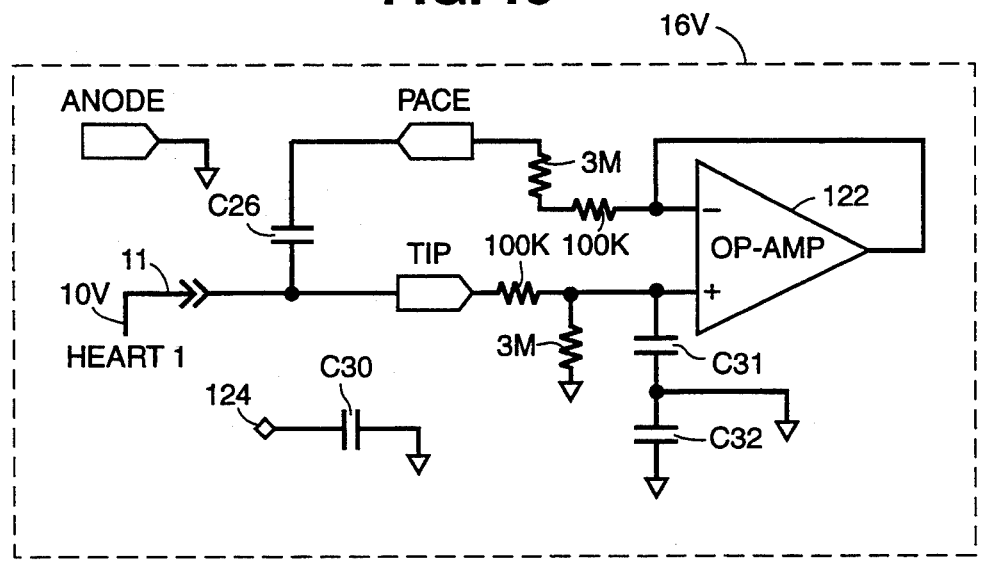

Following the active post charge phase, the output power capability of the operational amplifier 122 is restored to its standard level by opening the switch SW22 in a "boost turn off" operation shown by the pace/sense analog channel circuit 16V of FIG. 13 and the switch settings of the boost turn off row of FIG. 6. This operation allows the operational amplifier 122 to recover for about 300 ms after the amplifier boost ends.

Figure 14:
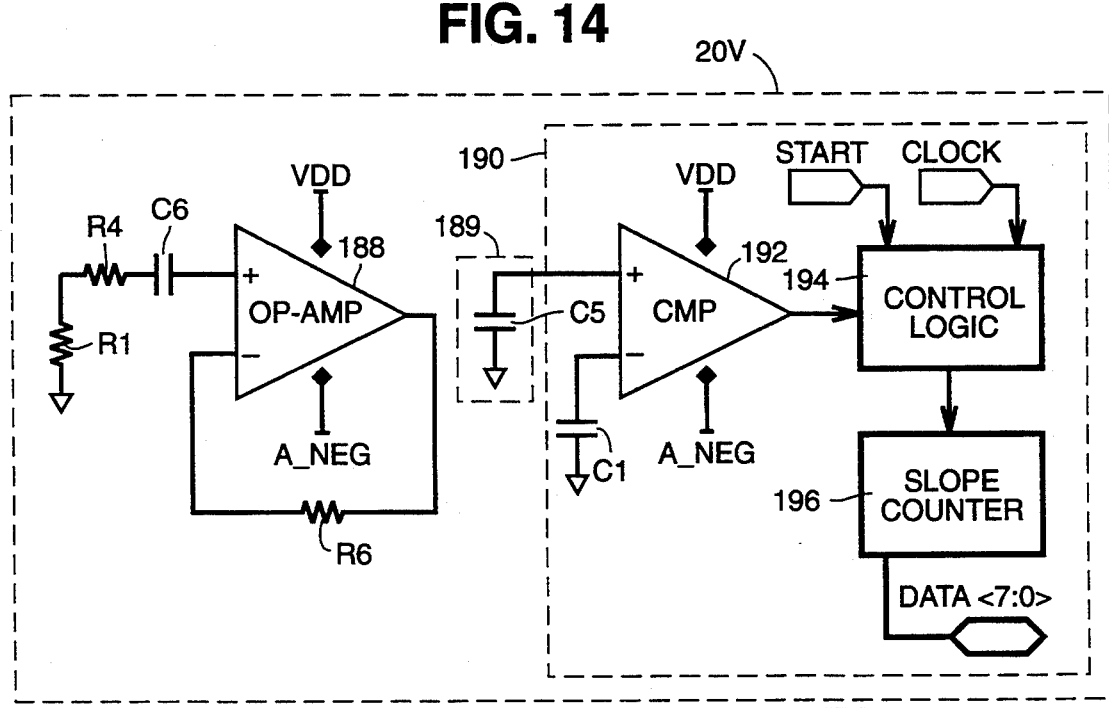
FIGS. 14–16 depict the status of components in the circuit of FIG. 5 when the switches in FIG. 5 are activated in accordance with the table of FIG. 6 during further additional different phases of operation.

At this point in the lead impedance measurement operation, the stimulation pulse has been delivered and the pace/sense analog channel circuit 16V of FIG. 4 is not required to perform further operations. The data acquisition channel circuit 20V of FIG. 5 now is activated to finish the lead impedance measurement. As shown in FIG. 14 and FIG. 6, the data acquisition channel circuit 20V performs a "warm-up" operation as the interface controller 15 of FIG. 2 activates the amplifier 188, the comparator 192 and the slope converter 190 by closing switches SWM21, SWM29, SWM30 and SWM23, as shown in the warm-up row of FIG. 6. The switch SWM29 is closed at this time to charge the slope capacitor C1 via current source 198. The interface controller 15 allows the warm-up phase to last a predetermined duration, for example, about 200 μs.

Figure 15:
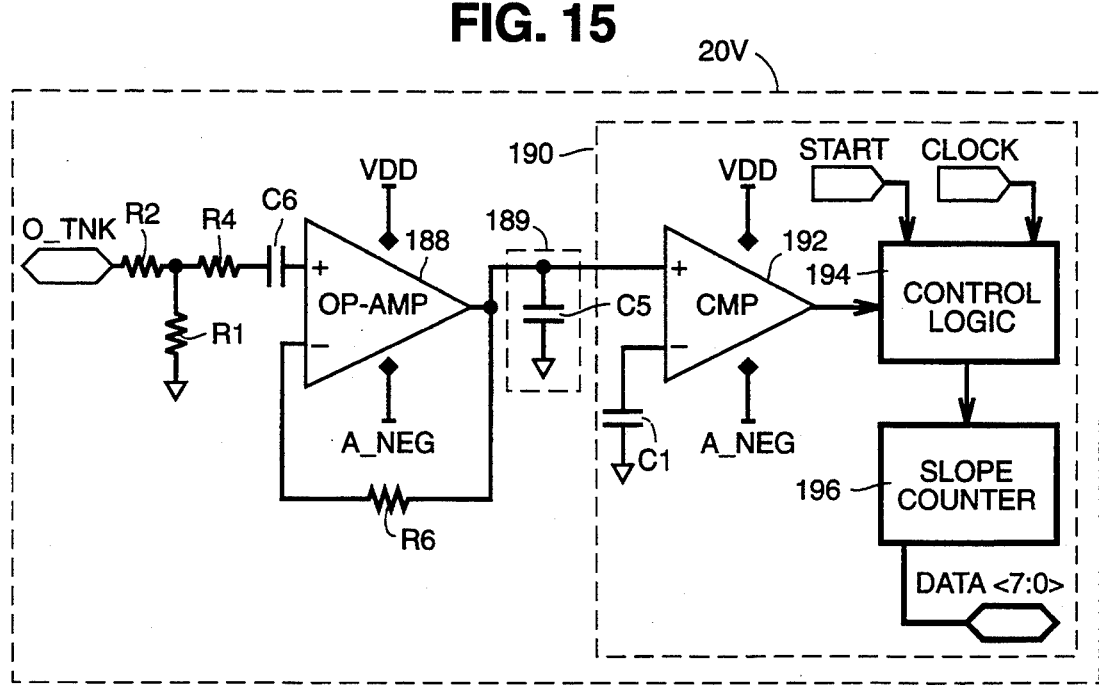

Following the warm-up operation, in a "delta sample" operation shown in FIG. 15 and the delta sample row of FIG. 6, the data acquisition channel 20V senses a second sample (after the first sample occurring during the sample/disconnect tip operation), subtracts the second sample value from the first sample value, and stores the result on capacitor C5 as Vs. The interface controller 15 activates the delta sample operation as it closes switch SWM8 to connect the current voltage on the tank capacitor (not shown), output potential O_TNK, onto capacitor C6. The switch SWM22 is closed to sample the output of the operational amplifier 188, which has its plus input connected to capacitor C6, onto the capacitor C5. The interface controller 15 controls the duration of the sampling operation so that it lasts a sufficient time, for example about 30 μs, to charge the capacitor C5. The potential Vs stored on the capacitor C5 is set in accordance with equation (3):

$$VS = -VO - O_{TNKa}*(R1/(R1+R2)) = (O_{TNKb} - O_{TNKa})*(R1/(R1+R2)) \quad (3)$$

where $O_{TNKa}$ is the output tank capacitor voltage after pacing.

Figure 16:
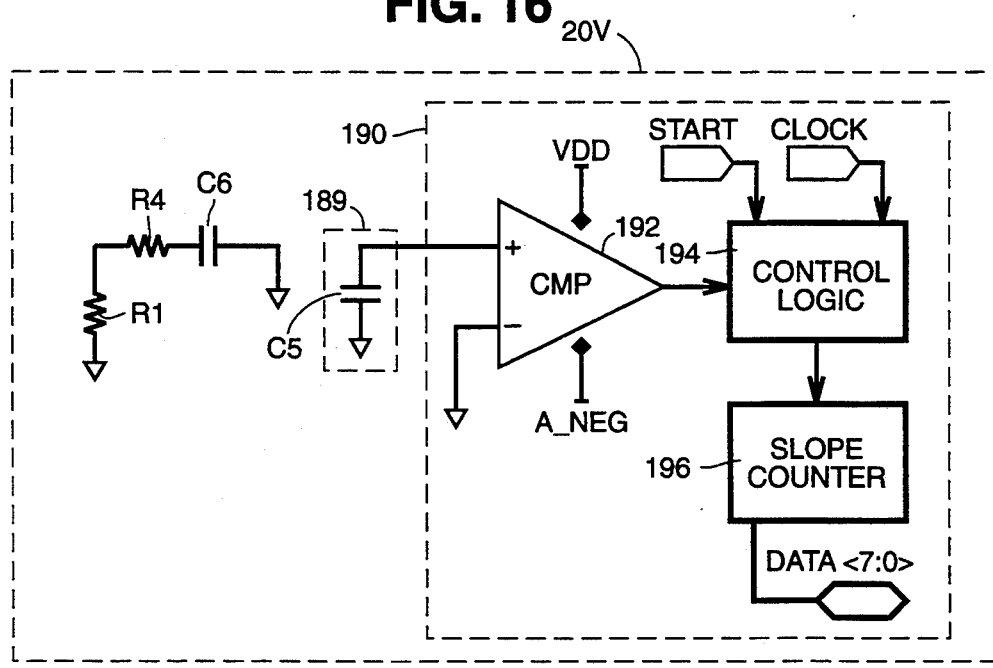

The resulting lead impedance measurement on the capacitor C5 is then converted into a digital form for use by the controller 28 in a "convert" operation. The data acquisition channel circuit 16V that is active during the convert operation is shown in FIG. 16 and in the convert row of FIG. 6. The interface controller 15 opens the switch SWM8 to disconnect the operational amplifier 188 from the output potential O_TNK and opens switches SWM21 and SWM22, deactivating the operational amplifier 188 and disconnecting its output from the storage capacitor C5. Switches SWM23 and SWM30 remain closed, connecting the output from the storage capacitor C5 to the slope converter 190, and switch SWM29 remains closed, charging slope capacitor C1, while the comparator 192 remains powered. A switch SWM28 remains open to allow the slope capacitor C1 to charge. The convert operation is held while the data conversion is made (e.g., for about 7 ms). After the convert operation, the pace/sense analog circuit 16V and the data acquisition circuit 20V return to sensing cardiac signals in the ventricular channel and the switch SWM28 is closed to discharge the slope capacitor C1, as shown by the bottom and top sensing rows of FIG. 6.

From the foregoing discussion, it is apparent that the present invention provides a method and apparatus for safely and reliably determining whether the polarity setting of an implantable stimulation device is consistent with the polarity of an attached lead while continuously supporting a patient with stimulation pulses.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

We claim:

1. A self-diagnostic lead polarity test system within a stimulating device that is implantable in a patient's body, said device being adapted to operate in a bipolar mode and in a unipolar mode and said device being adapted to receive an implanted stimulating lead having at least one electrode, each of said at least one electrodes having an electrical impedance relative to the patient's body, said system being adapted to recognize whether said electrode lead is bipolar or unipolar and being adapted to determine whether an electrode is functional, said system comprising:

a stimulating pulse generator for generating and applying stimulating pulses of predetermined pulse width to said stimulating lead;

means operable during the generation of a stimulating pulse by said pulse generator for acquiring a measurement relating to lead impedance;

means for storing externally-generated parameter values relating to lead impedance measurements which identify whether the electrode type of the lead is unipolar or bipolar and which indicate whether each of said at least one electrodes is functional;

a controller comprising means for controlling said pulse generator to generate a stimulating pulse and to take a lead impedance measurement while operating in the bipolar mode, means for comparing the bipolar lead impedance measurement to said stored parameter values to determine polarity and functionality of the electrodes, means operable when the lead electrode type is bipolar and the bipolar lead is functional for controlling the device to operate in a bipolar mode, means operable when the lead electrode type is unipolar and the unipolar lead is functional for changing the device operating mode from bipolar to unipolar, means for timing a predetermined interval following the generation of a bipolar mode stimulating pulse, and means operative at the end of said interval for controlling said pulse generator to generate a backup stimulating pulse while operating in the unipolar mode; and means for reporting whether the electrode type of the lead is unipolar or bipolar and whether each of said at least one electrodes is functional.

2. A system in accordance with claim 1, including a stimulating pulse power source for providing pulse power to said pulse generator at a predetermined voltage, wherein said lead impedance measurement acquiring means further comprises:

means for measuring a first voltage of said power source prior to delivery of a stimulating pulse by said pulse generator;

means for measuring a second voltage of said power source after delivery of the stimulating pulse by said pulse generator;

means for determining the difference between said first voltage and said second voltage; and means for converting the voltage difference to a measurement of lead impedance.

3. A system in accordance with claim 2, wherein said stimulating pulse power source is an output tank capacitor having a capacitance C, said stimulating pulse generator applies stimulating pulses for a predetermined pulse width T, said first voltage is V1, said second voltage is V2 and said lead impedance measurement R is derived in accordance with the following equation:

$$R = -T/(C*\ln(1-(V2-V1)/V_o)).$$

4. A system in accordance with claim 3, wherein said means for comparing the bipolar lead impedance measurement to said parameter values to determine polarity and functionality of the electrodes further comprises means for detecting a functional electrode when said lead impedance measurement is smaller than a prescribed impedance value.

5. A system in accordance with claim 4, wherein the device is a dual-chamber heart stimulating device including said stimulating pulse generator, said measurement acquiring means, said storing means, said controller, said reporting means and said power source for each of an atrial channel and a ventricular channel.

6. A system in accordance with claim 5, wherein the output tank capacitor in said ventricular channel power source has a larger capacitance than the output tank capacitor in said atrial channel power source.

7. A system in accordance with claim 1, wherein said means for timing a predetermined interval following the generation of the bipolar mode stimulating pulse and prior to the generation of a backup unipolar mode stimulating pulse times an interval in the range of from about 30 ms to about 150 ms.

8. A system in accordance with claim 7, wherein said means for timing a predetermined interval following the generation of the bipolar mode stimulating pulse and prior to the generation of a backup unipolar mode stimulating pulse is adapted to time an interval of approximately 100 ms.

9. A system in accordance with claim 1, wherein said externally-generated parameter values relating to lead impedance measurements identify that an electrode is present and functional when the lead impedance is smaller than a threshold value in the range of from about 1000 ohms to about 3000 ohms.

10. A system in accordance with claim 9, wherein said externally-generated parameter values relating to lead impedance measurements identify that an electrode is present and functional when the lead impedance is smaller than a threshold value of about 2000 ohms.

11. A system in accordance with claim 1, wherein when the functional lead electrode type is other than bipolar, said controller further comprises means operable subsequent to the delivery of the unipolar backup pulse for thereafter controlling the device to operate in a unipolar mode.

12. A system in accordance with claim 1, wherein said reporting means further comprises means for storing an indication of lead polarity, means for storing an indication of electrode functionality and means for storing lead impedance measurements.

13. A system in accordance with claim 1, wherein said reporting means further comprises telemetric communication means for transmitting diagnostic information to an external communicating device.

14. A method for measuring lead polarity within an stimulating device that is implantable in a patient's body, the device being adapted to operate in a bipolar mode and in a unipolar mode and the device being adapted to receive an implanted stimulating lead having at least one electrode, each of the at least one electrodes having an electrical impedance relative to the patient's body, said method being adapted to recognize whether the electrode lead is bipolar or unipolar and being adapted to determine whether an electrode is functional, said method comprising the steps of:

storing externally-generated parameter values relating to lead impedance measurements which identify whether the electrode type of the lead is unipolar or bipolar and which indicate whether each of the at least one electrodes is functional;

generating and applying stimulating pulses of predetermined pulse width to the stimulating lead;

acquiring a measurement relating to lead impedance during the generation of a stimulating pulse;

controlling said pulse generating and applying step to generate a stimulating pulse and to take a lead impedance measurement while operating in the bipolar mode;

comparing the bipolar lead impedance measurement to the stored parameter values to determine polarity and functionality of the electrodes;

controlling the device to operate in a bipolar mode when the lead electrode type is bipolar and the bipolar lead is functional and, when the lead electrode type is unipolar and the unipolar lead is functional, changing the device operating mode from bipolar to unipolar, timing a predetermined interval following the generation of the bipolar mode stimulating pulse, and controlling the pulse generating and applying step to generate a backup stimulating pulse following said interval while operating in the unipolar mode; and reporting whether the electrode type of the lead is unipolar or bipolar and indicating whether each of the at least one electrodes is functional.

15. A method in accordance with claim 14, wherein the device further includes a stimulating pulse power source for providing pulse power to the pulse generator at a predetermined voltage, and wherein said lead impedance measurement acquiring step further comprises the sub-steps of:

measuring a first voltage of the power source prior to delivery of a stimulating pulse by said pulse generating and applying step;

measuring a second voltage of the power source after delivery of the stimulating pulse by said pulse generating and applying step;

determining the difference between the first measured voltage and the second measured voltage; and converting the voltage difference to a measurement of lead impedance.

16. A method in accordance with claim 15, wherein the stimulating pulse power source is an output tank capacitor having a capacitance C, said stimulating pulse generating and applying step applies stimulating pulses for a predetermined pulse width T, the first voltage is V1, the second voltage is V2 and wherein said step of controlling the pulse generating and applying step includes the sub-step of deriving the lead impedance measurement R in accordance with the following equation:

$$R = -T/(C*\ln(1-(V2-V1)/V_o)).$$

17. A method in accordance with claim 16, wherein said step of comparing the bipolar lead impedance measurement to the parameter values to determine polarity and functionality of the electrodes further comprises the step of detecting a functional electrode when the lead impedance measurement is smaller than a prescribed impedance value.

18. A method in accordance with claim 14, wherein said step of timing a predetermined interval following the generation of the bipolar mode stimulating pulse and prior to the generation of a backup unipolar mode stimulating pulse includes the sub-step of timing an interval in the range from about 30 ms to about 150 ms.

19. A method in accordance with claim 14, wherein the step of storing externally-generated parameter values relating to lead impedance measurements includes the sub-step of identifying that an electrode is present and functional when the lead impedance is smaller than a threshold value in the range from about 1000 ohms to about 3000 ohms.

20. A method in accordance with claim 14, wherein when the functional lead electrode type is other than bipolar, said step of controlling the pulse generating and applying step to generate a back up stimulating pulse includes the sub-step, operable subsequent to the delivery of the unipolar backup pulse, of thereafter controlling the device to operate in a unipolar mode.

21. A method in accordance with claim 14, wherein said reporting step further comprises the sub-steps of storing an indication of lead polarity, storing an indication of electrode functionality and storing lead impedance measurements.

22. A method in accordance with claim 14, wherein said reporting step further comprises the sub-step of transmitting diagnostic information to an external communicating device via telemetric communication.

* * * * *